United States Patent [19]

Chulay, deceased et al.

[11] Patent Number: 4,941,868
[45] Date of Patent: Jul. 17, 1990

[54] OPTIMUM CENTRIFUGAL SEPARATION OF PARTICLES BY TRANSIENT ANALYSIS AND FEEDBACK

[75] Inventors: Steven J. Chulay, deceased, late of Woodside, Calif., by Viktoria D. Chulay, trustee; Allen P. Minton, Bethesda, Md.; Robert Giebeler, Cupertino, Calif.

[73] Assignee: Beckman Instruments, Inc., Fullerton, Calif.

[21] Appl. No.: 379,261

[22] Filed: Jul. 10, 1989

[51] Int. Cl.$^5$ .............................................. B04B 13/00
[52] U.S. Cl. ....................................... 494/37; 494/10; 494/11
[58] Field of Search ...................... 494/10, 11, 37, 7, 1, 494/85, 16; 422/72, 100, 102; 210/781, 782

[56] References Cited

U.S. PATENT DOCUMENTS 4,244,513  1/1981  Fayer ..................................... 494/38
4,285,810  8/1981  Kirkland .............................. 494/10

OTHER PUBLICATIONS

"Rapid Purification of Plasmid DNA By A Single Centrifugation in a Two-Step Cesium Chloride Gradient", *Biochemical and Biomedical Research Communication*, vol. 117, No. 3, Dec. 29, 1983, p. 835.

"Simulation of Gradient and Band Propagation in the Centrifuge", Sartory, et al., *Biophysical Chemistry*, 5 (1976), 107–135.

"Computer Simulation of Density-Gradient Centrifugation", Steensgaard, et al., *Subcellular Biochemistry*, vol. 6, 1979, pp. 117–141.

Primary Examiner—Robert W. Jenkins
Attorney, Agent, or Firm—William H. May; Paul R. Harder; Wen Liu

[57] ABSTRACT

A process and apparatus for predicting the time and position dependent concentration of macromolecules of differing species in a gradient forming solution during centrifugation is disclosed. A mathematical model of the time dependent behavior of gradient forming solutes in a centrifugal field, based upon the underlying physical principles governing sedimentation and diffusion is formulated. The simplifying approximation is made that the wall effects may be ignored, and that the transport of solute may be treated as a one dimensional process with forces dependent only upon the radial distance. A sedimentation diffusion (Lamm) equation in one dimension is numerically integrated. The sedimentation diffusion equation (Lamm equation) for each macrosolute is solved concurrently with that for the gradient forming solute, utilizing the experimentally based density dependent sedimentation coefficient. The equations are solved for incremental time periods for the centrifuged samples in successive radial segments. The equations use concentration dependent values of sedimentation and diffusion coefficients of gradient forming solutes. There is obtained the time and position dependence of the concentration of both gradient-forming solutes and macrosolutes at a fixed temperature for an arbitrarily specified starting concentrations of the density forming solute. The distribution of the macromolecule follows from distribution of the gradient forming solute for each time period and each radial slice.

7 Claims, 4 Drawing Sheets

Microfiche Appendix Included
(66 Microfiche, 3 Pages)

OPTIMUM CENTRIFUGAL SEPARATION OF PARTICLES BY TRANSIENT ANALYSIS AND FEEDBACK

MICROFICHE APPENDIX

A microfiche appendix consisting of 66 frames on 3 fiches is filed herewith.

This invention relates to the behavior of macromolecules in density gradient-forming solutions during centrifugation. More specifically, a process including prediction of the time-and position-dependent concentration of macromolecules in a density gradient-forming solution is disclosed.

BACKGROUND OF THE INVENTION

A widely used technique for separation of biological macromolecules in solution (macrosolutes), known as isopycnic density gradient separation, involves high-speed centrifugation of the macrosolutes at relatively low concentration together with a small solute, referred to as the gradient-forming solute at high concentration. The density gradient, arising from the concentration gradient of the concentrated small solute, may be preformed or may be self-forming under the influence of the centrifugal field. Gradient-forming solutes of choice for the self-forming gradient experiment are heavy salts such as chlorides, bromides, or iodides, as concentrated solutions of these have low viscosity, permitting (relatively) rapid gradient formation. As the density gradient is formed, each macrosolute migrates to form a band at the particular position in the density gradient corresponding to its buoyant density, i.e., that position where the applied centrifugal force is exactly cancelled by the buoyant force. The method works well, but suffers from two major disadvantages: [a] As conventionally performed the sample is centrifuged until an equilibrium distribution of the gradient-forming
solute is achieved (up to 24 hours and sometimes longer) to assure the desired separation of macrosolutes. [b] Rotor velocity and hence speed of separation, are limited by the condition that the solution of the gradient-forming salt not attain saturation exceeded at the bottom (or outer edge) of the tubes at any time during centrifugation, so as to avoid the possibility of salt precipitation, which might overstress and damage the rotor or otherwise defeat the purpose of separation.

This disclosure is motivated by the desire to develop new kinds of time-saving density gradient separations and to optimize the conditions under which conventional density gradient separations are performed so as to obtain the desired separation in as short a time as possible.

Prior Art

[A] Experimental

In an effort to shorten run times and improve volumetric separation between bands, O. M. Griffith et al. developed the Rapid Purification of Plasmid DNA by a Single Centrifugation in a Two-Step Cesium Chloride Gradient reported in Biochemical and Biomedical Research Communication. Dec. 29, 1983. pg. 835. For plasmid DNA separations this reference utilized following features:

(1) Relatively high-speed rotors with tubes loaded with a preformed stepped CsCl gradient which collectively contribute to a more rapid approach to equilibrium: and (2) After running at a relatively high speed limited by the average density of the liquid loads the speed is reduced, to allow the salt gradient to become shallower and provide better volumetric separation between bands.

Another reason for reduced speed is to avoid any salt precipitation during the high-speed operations that could induce rotor stress above design values. The run times were determined empirically by making runs of varying duration. The shortest run time giving acceptable results was chosen.

B Theoretical simulation of band migration

Sartory et al., Biophys. Chem. 5 107; 1976, presented a method for calculating the distributions of gradient forming solute and macrosolute as a function of time. The method is applicable only when the macrosolute distribution may be represented as a symmetrical band. The equations used by Sartory et al. are very different, and far more complex, than those used in the present disclosure. The numeric solution of their equations would seem to require much more computation than the present method, and probably could not be performed conveniently on a PC-type microcomputer. They did not publish results showing the evolution of either band shape or position with time. Steensgaard and Moller (Subcellular Biochemistry, vol. 6 pp. 117–141 D. B. Roodyn. ed., Plenum. N.Y., 1979) have simulated time-dependent solute migration in a time-invariant sucrose gradient during centrifugation. They did not simultaneously simulate transient changes in both solute and gradient material during centrifugation.

Minton and subsequently Chatelier and Minton, have previously developed methods for rapid simulation of the sedimentation behavior of non-interacting and interacting macrosolutes in the absence of a density gradient-forming solute. These methods are in the public domain. These methods are confined to the behavior of macromolecules alone in the centrifugal field. Gradient forming solutes and the interaction of molecules herewith are not treated.

SUMMARY OF THE INVENTION

A process and apparatus for predicting the time-and position-dependent concentration of macromolecules of differing species in a gradient-forming solution during centrifugation is disclosed. A mathematical model of the time-dependent behavior of gradient forming macromolecular solutes in a centrifugal field based upon the underlying physical principles governing sedimentation and diffusion of each species, is formulated. Empirical functions describing the concentration dependence of the diffusion coefficient, the activity coefficient, and the solution density at a fixed temperature are obtained from known data. The assumption is made that the frictional coefficients for sedimentation and diffusion are equal at finite concentrations. The simplifying approximation is made that the wall effects may be ignored, and that the transport of solute may be treated as a one dimensional process with forces dependent only upon the radial distance. A sedimentation diffusion (Lamm) equation in one dimension is numerically integrated. It is assumed that the macromolecules do not interact, one with another. It is further assumed that each macromolecule interacts with the gradient-forming solute only through the buoyancy factor. The sedimentation diffusion equation (Lamm equation) for each macrosolute is solved concurrently with that for the gradient-forming solute utilizing the experimentally based density-dependent sedimentation coefficient. The equations are solved for incremental time periods for the centrifuged sample in successive radial segments. The equations use concentration dependent values of sedimentation and diffusion coefficients of the gradient forming solutes. There is obtained the time and position dependence of solute concentrations at a fixed temperature for arbitrarily specified initial distributions of all solutes. By the expedient of rapid iteration of mathematical solution, with each successive iteration utilizing quantitative results obtained in previous iterations a quantitative mathematical model and derived map of the time-and position-dependent centrifugation process is obtained in advance of actual centrifugation. The resulting mathematical solution and derived map can be utilized by a researcher to predict desired separation time and the position of the macrosolute within the cell well before the gradient-forming solute reaches equilibrium. Initial centrifugal fields which might ultimately result in rotor-damaging precipitations of the gradient-forming solute can be used to accelerate gradient formation, and the centrifugal field reduced prior to precipitation. By the expedient of utilizing the disclosed computer model to predict both time of separation and cell position of macromolecular solutes, the researcher can terminate centrifugation in the shortest possible time, often a time period considerably less than the equilibrium condition preferred in the prior art. A computer program is disclosed.

Other Objects, Features and Advantages

An object of this invention is to provide the researcher with an effective simulation on a computer of the physical interaction of gradients and solutes within a centrifuge tube, the simulation allowing preparative planning for ultracentrifugation. Accordingly, a computer simulation of actual laboratory centrifugation is provided. The computer simulation is fast. The operator, utilizing the results of the simulation, can terminate the laboratory centrifugation as soon as the macromolecules are separated.

An advantage of the disclosed program utilized as a planning protocol for ultracentrifugation is that time of centrifuge operation is saved. Trial and error iterations required in the prior art are not required.

An additional advantage is that the purity of the end products can be varied at the discretion of the researcher. The researcher can await complete separation. Alternatively, less than complete separation can be effected. The time of centrifugation need only proceed to the desired end product purity.

Yet an additional advantage is that the program is readily adaptable to differing centrifuge rotors.

A further advantage of this invention is that the disclosed apparatus and process is applicable to all classes of solvents and materials soluble in those solvents. Although water soluble solutes are more commonly used, other classes of solutes and applicable nonaqueous solvents may as well be used.

An additional advantage of the disclosed protocol and computer program is that for the first time it is possible to accurately model the progress of the separation within a centrifuge. It is not required that an actual view of separation within an analytical centrifuge rotor be obtained; it is further not required that a preparative centrifuge rotor be stopped and the sample cell be opened and fractionated.

Yet another advantage is that the program is readily adaptable to the initial positions of the macromolecules in the density gradient-forming solute. Such macromolecules can be originally uniformly distributed or alternatively positioned as discrete layers.

A further object of this invention is to rapidly develop a density gradient. According to this aspect of the invention, the centrifuge is initially run at a speed that would ultimately precipitate out of the solution the gradient forming solute. Running proceeds to a time where the disclosed program predicts that a local concentration in the cell increases to where precipitation is likely. Before this precipitation concentration is reached, the speed of centrifugation is reduced. It is successively reduced to a level where a concentration resulting in solute precipitation is never reached.

An advantage of this aspect of the invention is that the formation of the density gradient can be accelerated. Consequently, the desired separation can likewise be accelerated.

A further advantage of this aspect of the invention is that no danger of solute precipitation with possible rotor damage need occur. Instead, the rotor can be used optimally to generate the required density gradient on an accelerated basis up to, but not beyond solute precipitation.

An additional aspect of this invention is that the experimental results obtained in a centrifuge run partially to a state of solute equilibrium can be utilized to predict the physical properties of the materials classified. While such use of the disclosed program is not the primary utility of this disclosure, such a result is obtainable with the disclosed apparatus and process.

DESCRIPTION OF THE PREFERRED EMBODIMENTS

Figure 1:
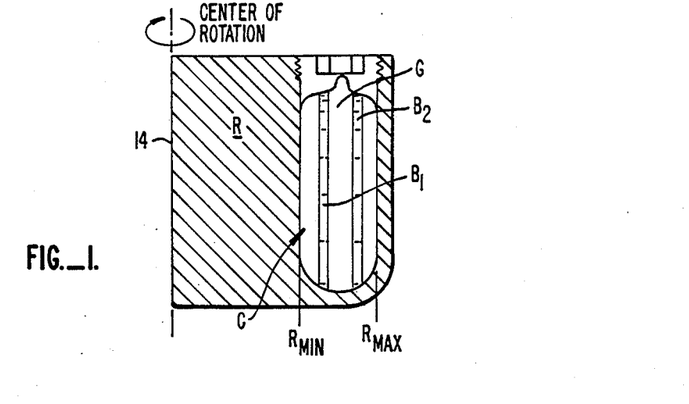
FIG. 1 is a schematic of a preparative centrifuge rotor cross section illustrating a cylindrical sample tube placed with its vertical axis displaced from and parallel to the rotor axis, the tube including separation of macromolecules in two discrete bands within a gradient forming material.

Referring to FIG. 1 a preparative rotor R is schematically illustrated spinning about a center of rotation 14. A sealed cylindrical tube C containing a gradient forming material G and separated macromolecules B1 and B2 is illustrated. The tube includes radii Rmin and Rmax from the center of rotation 14.

It will be understood that this disclosure is also applicable to analytical centrifuges. Analytical centrifuges include a sector-shaped cell having top and bottom windows permitting observation during centrifugation.

Figure 2:
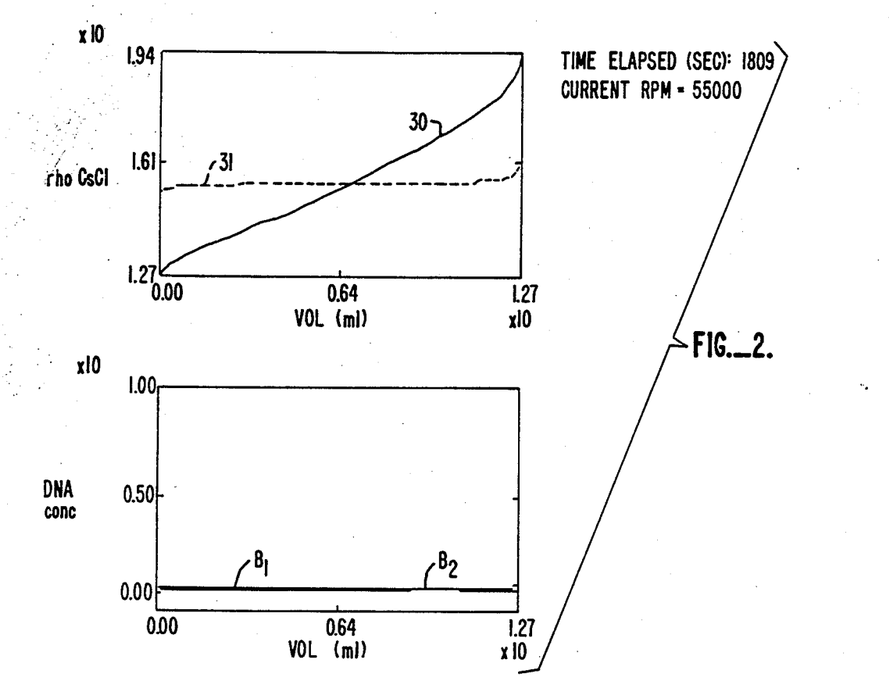
FIG. 2 is a diagram of an actual computer simulation illustrating the gradient forming solution shortly after centrifugation has commenced with the sample just beginning to undergo separation.

Referring to FIG. 2 a computer printout of two functions is illustrated. This computer generated figure is a half hour into the simulated centrifugation. Referring to the upper screen it will be seen that the line 30 indicates the eventual equilibrium density gradient of the density gradient-forming solute in the solution. Here the solvent is water. The gradient forming solute is cesium chloride (CsCl). The indication 30 indicates the density formed by the CsCl at equilibrium. At the end of one-half hour, the actual density gradient will be indicated by line 31.

Below the plot of the density gradient, there can be seen a plot of the distribution of the macrosolutes. Here the respective macrosolutes B1 and B2 are uniformly distributed along the length of the cell.

Figure 3:
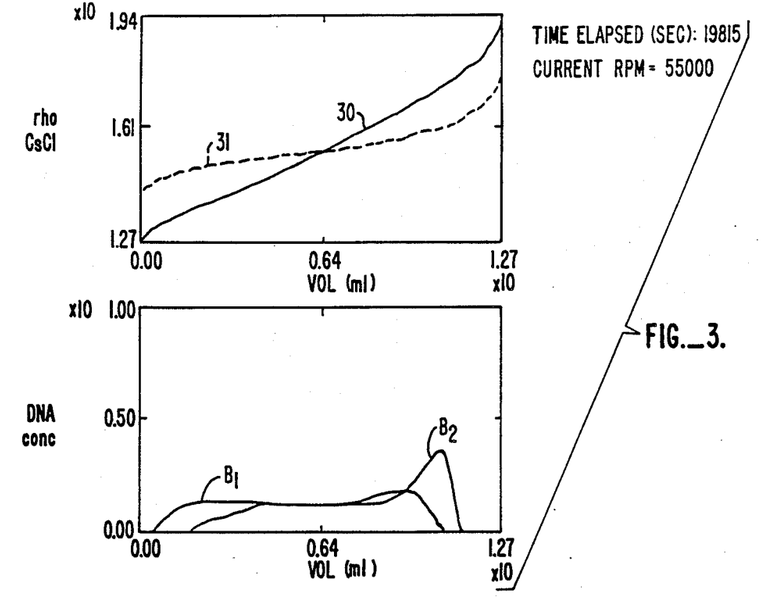
FIG. 3 is a view similar to FIG. 2 at a later time during centrifugation, with the gradient forming solution beginning to form its gradient and the paired macromolecules beginning their process of separation.

Referring to FIG. 3 separation is shown some 5 ½ hours into the computer simulated centrifuge run. It can be seen at this time that the actual gradient 31 has begun to move to and towards the equilibrium gradient 30.

Referring to the lower screen it can be seen that macromolecule B1 is beginning to separate from macromolecule B2.

Figure 4:
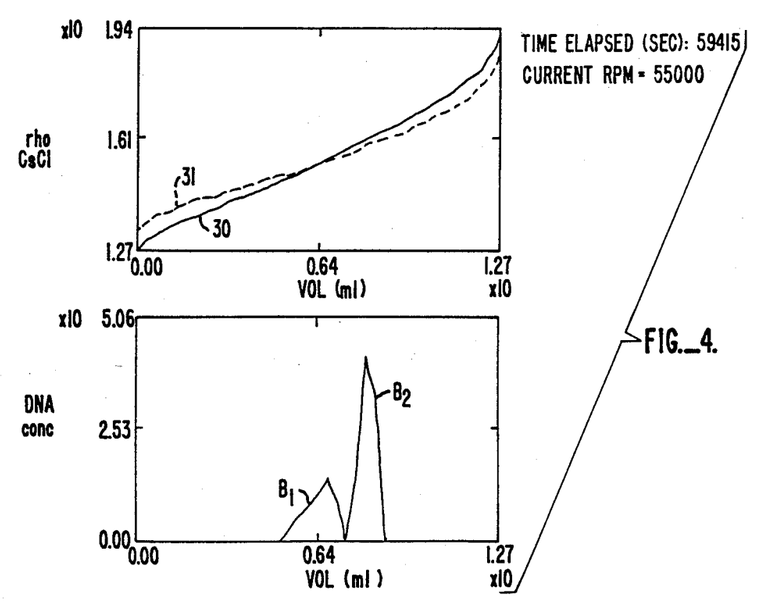
FIG. 4 illustrates the centrifugation at an even later time, with the achievement of complete separation of the macromolecules, and the gradient-forming solution approaching equilibrium.

Referring to FIG. 4 a plot is shown 17 hours into the computer run. At this time, the actual density gradient 31 more closely approaches the ultimate equilibrium density gradient 30. At the same time, the solutes B1, B2 have for the first time become completely separated.

Assuming that separation of the species is desired, it can be understood that the process of centrifugation could be stopped at this time. Further centrifugation can widen the separation and further concentrate the species. Centrifugation to equilibration need not occur.

Figure 5:
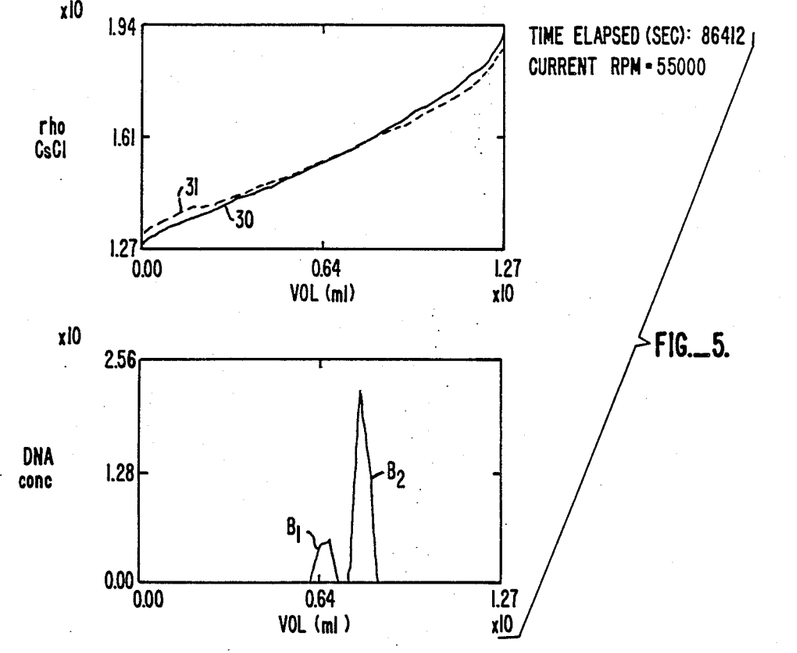
FIG. 5 is a view similar to FIG. 4 showing the gradient forming solution at approximate equilibrium with the effective equilibrium separation illustrated at the end of a 24 hour period, it being noted that 7 hrs. of centrifugation can effectively be avoided utilizing the current invention and terminating centrifugation at the predicted separation time illustrated in FIG. 4.

Referring to FIG. 5 the centrifugation process is shown at the end of the 24 period. It can be seen that the distribution of gradient former closely approaches the equilibrium state.

At the same time, it will be recognized that very little additional separation has occurred between the macromolecules B1, B2 from that separation shown in FIG. 4. This being the case, it can be understood that substantially no quantifiable improvement has been obtained in the succeeding hours of centrifugation.

It will be understood that an operator, as a postoperative step at the end of the state indicated by FIG. 4. may well desire to cease centrifugation.

Figure 6:
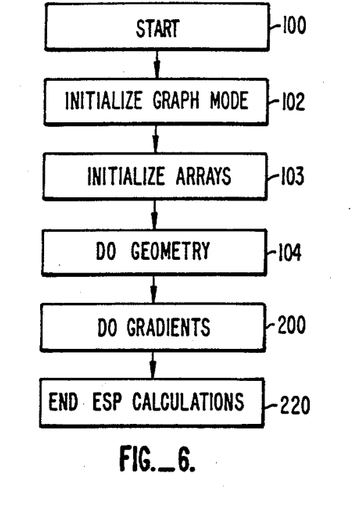
FIG. 6 is a block diagram of the flow chart of the overall program.
Figure 7:
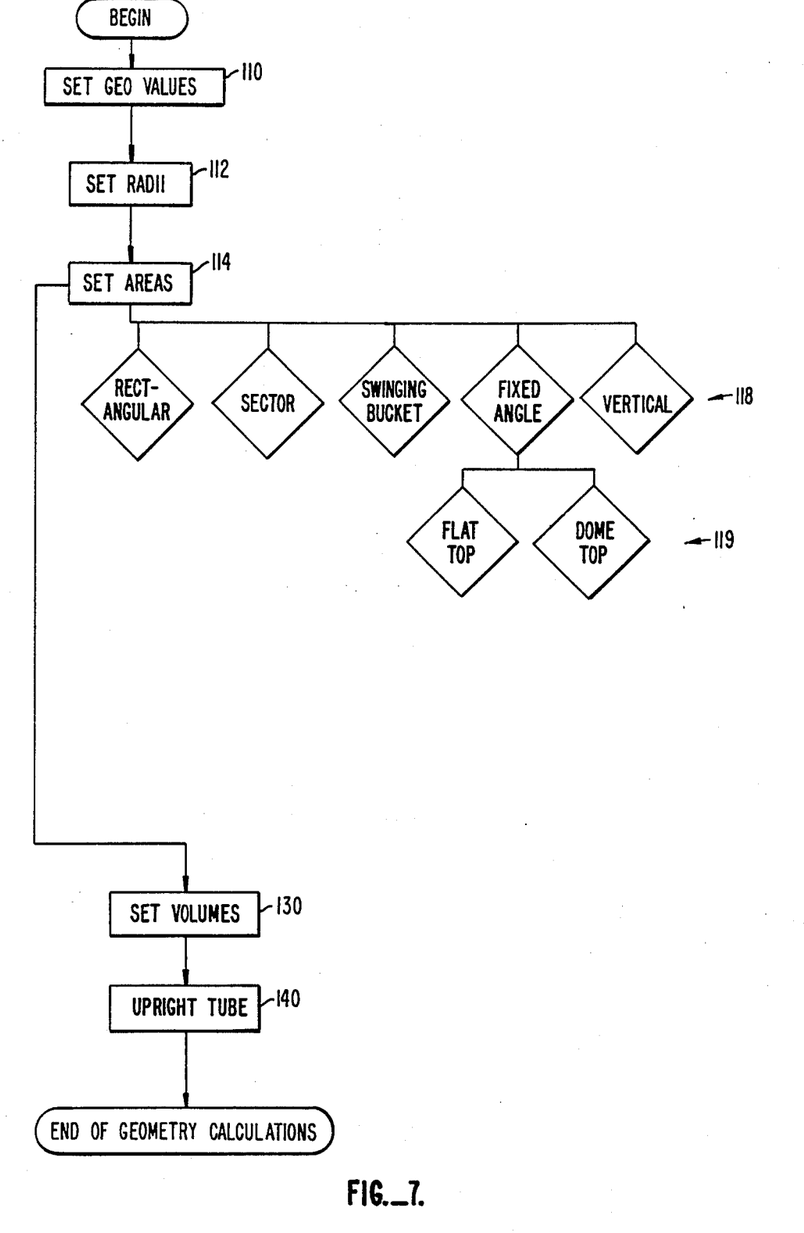
FIG. 7 is a flow chart setting forth the geometry calculations the geometry illustrating how the program can be conformed to various rotor configurations.

Further, and with reference to FIGS. 6 and 7, the overall operation of the program, as well as its adaption to rotors of various configurations, can now be discussed.

The gradient forming material forms a variable density gradient dependent upon the time and centrifugal field. The field varies directly as the distance from the center of rotation. Assuming, in the case of FIG. 1 two macromolecules are present, over a period of time the respective bands B1 and B2 form in the tube C. These respective bands are the product of two opposing forces within the gradient field.

The first force relates to sedimentation. This force causes the material to move relative to the spin axis. Second, and opposing the force of sedimentation, is the force of diffusion. This force would maintain an equal distribution of the materials within the cell in the absence of the centrifugal field.

As will hereinafter be set forth, the purpose of this invention is to simulate centrifugation. From this simulation many useful results can follow. These results can include:

(1) Optimization of run time;

(2) Time and position dependent information of the separated component(s).

(3) Comparison of the actual distribution of the species with the simulated distribution of the species.

As an example of the type of comparison that this invention makes possible, the predicted behavior of macromolecules could be compared with the actual behavior of macromolecules in an analytical ultracentrifuge. For example, it could be assumed for the purpose of the centrifugation that molecules are simple noninteracting hydrodynamic spheres. Divergence of the actual results from the simulation could indicate the assumption is in error. Other simulated conditions, such as differing molecule shapes or interaction of the molecules—one with respect to another—can thereafter be examined.

The reader should understand the difference between the sedimentation and the diffusion of molecules and the corresponding sedimentation coefficient and diffusion coefficient of the molecules. The sedimentation coefficient and diffusion coefficient are physical parameters of macromolecules. Sedimentation and diffusion describe the changes in concentration of the macromolecules due to the centrifugal field and concentration gradient, respectively. The movement of the macromolecules is a function of the coefficients and the experimental parameters that are used (rotor speed, temperature, gradient forming solute, etc.). This understanding can be gained by the solving of a Lamm equation.

We use estimates of the macromolecule's coefficients and theoretically model the actual sedimentation coefficient of the gradient forming solute.

The macrosolutes migrate to the density that is equal to their buoyant density in the cell. The macromolecules that are in a portion of the cell that has a gradient with a higher density will float inward to an area of equal buoyant density. This floatation will occur until the molecules become neutrally buoyant. The macromolecules that are in a portion of the cell that has a gradient with a lower density will sediment outwards to an area of equal buoyant density. This sedimentation will occur until the molecules become neutrally buoyant.

A computer model indicating separation is generated. This model is based on underlying physical principles governing sedimentation and diffusion of each of the species. The computer model predicts the time dependent concentration of the separating macromolecules. By utilizing the prediction optimum termination of the centrifugation process can occur enabling separation in the most efficient possible manner.

Having outlined the process, the description of the mathematical model may now be set forth.

[4b] Description of Mathematics Model

Kinetics of gradient formation

1. Density of the gradient former is linear in mass/volume concentration $$\rho(w) = \rho_o + (1 - \bar{V}\rho_o)w \qquad [1]$$

where $\rho$ is the solution density w is the weight/volume concentration of the solute, $\bar{v}$ is the partial specific volume of the gradient former and $\rho_o$ is the density of the solvent.

2. Empirical functions describing the concentration dependence of the thermodynamic activity coefficient $\gamma(w,T)$, and the diffusion coefficient, $D(w,T)$, at a fixed temperature T are obtained by modeling data obtained from experiment. From the function $\gamma(w,T)$ a second function $d\ln \gamma(w,T)/dw$ is derived.

3. Assuming that the frictional coefficients for sedimentation and diffusion are equal at finite concentrations, an apparent sedimentation coefficient of gradient former may be defined as a function of concentration:

$$s(w) = \frac{M[1 - v\rho(w)] \cdot D(w)}{vRT(1 + w \cdot d\ln\gamma/dw)} \qquad [2]$$

where M is the molecular weight of the gradient-forming solute, T is the absolute temperature R is the molar gas constant, and $v$ the degree of disassociation of the gradient former (for example, $v=2$ for a 1-1 salt, and $v=1$ for a nonionic solute). An empirical analytical expression for $s(w,T)$ is obtained by mathematical modeling of numerical results obtained using eqn [2].

4. The simplifying approximation is made that wall effects may be ignored, and that transport of solute may be treated as a one-dimensional process, i.e., forces are dependent only upon radial distance and are applied only in the radial direction. This assumption is exact for a sector-shaped cell, and is probably quite accurate for a cylindrical cell in a swinging bucket rotor. It is inaccurate, in principle, for fixed-angle and vertical rotors, but experimental tests performed to date of the predictions deriving from this assumption have not yet demonstrated major quantitative errors for either fixed-angle or vertical rotors. Thus the assumption appears to be useful in a practical sense.

It should be understood that extending this model to any complex tube orientation to theoretically represent "wall effects" in a non-equilibrium situation (with the exception of surface roughness effects) can be done by making the finite difference model 2- or 3-dimensional. It should further be understood that the computational time increases exponentially with the number of dimensions. The sedimentation-diffusion (Lamm) equation in one dimension is $$\frac{\partial w(r)}{\partial t} = -\frac{\partial}{\partial r}[A(r) \cdot (s\omega^2 r w(r) - D \cdot dw(r)/dr)]$$

where r is the radial distance, A(r) is the cross-section of the centrifuge tube, $\omega$ is the angular velocity of the rotor. The appropriate equation is numerically solved using time- and position-dependent values of $s(w,T)$, and $D(w,T)$, calculated as functions of the local concentration $w(r,T)$ as described above, to obtain the time and position-dependence of w and $\rho$ at temperature T for an arbitrarily specified starting gradient $w_o(r)$. The formulation of eqn [2] is such that if the numerical solution of the Lamm equation is accurate, the limiting form of the gradient of w at long time will correspond exactly to the equilibrium gradient.

Kinetics of macrosolute band formation

1. Estimates of the sedimentation coefficients and diffusion coefficients of each of the biospecies in the limit of low concentration in pure solvent (water) at the desired temperature are obtained either by direct experimental measurement, or via previously validated empirical functions relating (known) macromolecular size to (unknown) hydrodynamic properties.

Data describing the diffusion coefficient (D) for CsCl as a function of concentration (w) are obtained from the literature. These are published data (R. A. Robinson and R. H. Stokes. "Electrolyte Solutions", Academic Press, NY, 1959). We have applied the following empirical curve-fit to these data for purposes of the ESP program, $$D(w) = 1 \times 10^{-5} \times (1.74 + 0.262\exp[-3.62 \times 10^{-2}w] + 1.15 \times 10^{-3}w - 5.26 \times 10^{-7}w^2)$$

where w describes the concentration in gm/L.

Data describing the activity coefficient, $\gamma$, as a function of concentration are also taken from the Robinson and Stokes "Electrolyte Solutions." Data there published covers the range of concentrations up to about 800 gm/L.

These combined data were then fitted to a curve as a function of concentration as described, $$\gamma = [-Aw^{\frac{1}{2}}/[+Bw^{\frac{1}{2}}] + Cw + Dw^2]$$

where $A = 0.108628$ $B = 0.101993$. $C = 0.139734 \times 10^{-3}$, and $D = 0.279410 \times 10^{-6}$.

These activity coefficients were then used to determine the sedimentation coefficients of the salt as a function of concentration. The relationship between activity coefficient and sedimentation coefficient, S, is well known and is described in several texts. We calculated S at various concentrations. A curve fitting routine was used to obtain a simpler empirical relationship between S and the concentration, w is as follows:

$$\text{where } S(w) = S_0 - B_0 w - B_1 \exp(-B_w w)$$

where, $S_0 = 0.64986 \times 10^{-13}$, $B_0 = 0.375793 \times 10^{-16}$, $B_1 = 0.130128 \times 10^{-13}$, and $b_2 = 0.288990 \times 10^{-2}$.

2. For simplicity it is assumed that the macrosolutes do not self-interact or interact with each other. The simulation may be straightforwardly modified to take account of such interactions if experiment shows that they are not negligible under the conditions of the actual experiment.

3. It is assumed that each macrospecies interacts with the gradient-forming solute only through the buoyancy factor, yielding an effective sedimentation coefficient:

$$s(r) = s_o \frac{(1 - v\rho(r))}{(1 - v\rho_o)} \qquad [4]$$

Where $s_o$ is the actual sedimentation coefficient at limiting low concentration in pure solvent.

4. The sedimentation-diffusion equation for each macrosolute is solved concurrently with that for the gradient-forming solute, utilizing the effective (density dependent) sedimentation coefficient in place of the actual sedimentation coefficient. A viscosity correction to the sedimentation and diffusion coefficients is not required in salt solutions, but is likely to prove necessary when the calculations are extended to nonionic gradient-forming solutes such as glycerol or sucrose. Such a correction is straightforward and readily implemented.

The reader will understand the process of avoiding precipitation and minimizing the time required for separation. The speed of the rotor is maintained at the highest possible value consistent with rotor strength limitations, until just before gradient saturation concentration is reached at the bottom of the tube. At this time the speed is stepped down, resulting in a momentary fall in the gradient material concentration at the bottom of the tube. The size of each successive speed step is selected so that the subsequent drop in gradient material concentration at the base of the tube is minimal, not exceeding 5%. This process dramatically reduces the time required for separation (e.g., by as much as 50%). Typically 5 speed steps are used before separation is complete, at which time the speed has been reduced to where the existing transient and the ultimate equilibrium gradient distributions in proximity to the macromolecule bands near the middle of the tube are similar.

In a rotor in which 100% separation of macromolecules (yield) was desired in a single centrifugation conducted at a constant speed (52,000% RPM) where at equilibrium the gradient concentration does not exceed precipitation, 100% yield occurred at 18 hours, 49 minutes. The represents the most currently used equilibrium laboratory technique.

In a single centrifugation conducted at a constant speed (of 62,500 RPM). 100% yield occurred at 13 hours and 40 minutes.

Taking the same rotor and running it at two discrete speeds, it was first run for 2 hours and 90,000 prm. Running at this speed would ultimately induce rotor damaging precipitation.

Thereafter, the rotor was run for approximately 12 hours at 59,000 rpm. At 12 hours 48 minutes 100% yield was present. This demonstrates that a two speed centrifugation saves time.

Finally, a five step centrifugation protocol was utilized. The centrifuge was run for two hours at 90,000 rpm, the precipitation inducing speed. Thereafter, the speed of the rotor was stepped down in gradual step decreases. It was run for 50 minutes at 80,000 rpm, 2 hours at 70,000 rpm, 3 hours at 65,000 rpm and for the remainder of the time at 60,000 rpm.

One hundred percent yield occurred in 10 hours and 29 minutes into the protocol. It will be noted that this saves over 2 hours in total centrifugation time from the protocol of the two step run.

The reader will understand that without the program as herein set forth, trial and error on numerous samples would be required to get minimal run time to the desired separation. With the enclosed protocol, it is possible to predict in advance both time and cell fractionation location to obtain the desired separation of the species.

Filed concurrently herewith is a microfiche of a computer program. This program runs on an Apollo DN 3500 or DN 3000 minicomputer manufactured by the Apollo Computer Company of Chelmsford, Mass. This program will run on any Apollo computer that supports graphic calls and functions or graphic primitive routines. This software produces graphic similar to but not identical to the graphics herein illustrated. Graphics are obtained by using the program in conjunction with Seiko Hard Copier Model 5303 manufactured by the Seiko Corporation of Japan. This computer program is our preferred embodiment.

The program operates in accordance with the flowchart shown on FIG. 6. Specifically, and with respect to the start at 100, the user chooses a rotor for emulation. A simulation run is set.

Initially, the graphing function of the computer is initialized (see 102).

Thereafter, and as step 103, the user fills the work arrays with their initial values. These values include the starting concentration of gradient producing salt and the macromolecules together with the sedimentation and diffusion constants utilized.

At step 104, calculations applicable to the geometry are made which calculations are schematically set forth for a particular rotor on FIG. 7.

Referring to FIG. 7, the initial geometric values including the inner and outer radius, the cylindrical length and the like are set for a particular rotor (see 110). With respect to step 112, the discrete radius values utilized in making the incremental calculation set forth herein are established.

With respect to 114 and for each of the discrete radius values, area values for all simulated slices of the centrifuge tube must be calculated. The specific type of centrifuge rotor is selected in step 118 which in turn establishes the types of tubes that are selectable in step 19. The tubes can be either cylindrical or sector-shaped.

Once the areas have been determined the volume for each simulated slice of the centrifuge tube is computed at step 130.

Regarding step 140, where fixed angle and vertical rotors are utilized, the volumes of the horizontal slices must be recalculated when the tube is taken out of the centrifuge and the discrete layers realigned with the final vertical orientation of the tube. Once the completion of the geometry calculations are made, the main portion of the program continues.

At step 200, the gradients are calculated. Specifically, the successive concentration array values are calculated for each successive time step in the simulation.

Thereafter, the percent separation of the two components is calculated.

In order to prevent precipitation of the gradient forming salt, a check is made for precipitation. Interruption of the calculation is made at arbitrary run times to save the concentration data and draw a graph. Data sets from each run time can be arbitrarily selected and stored.

As a final step 220, the ten run time observations are saved in the system. The viewer can move forward and backwards through these data sets to view them as graphs and to view the separation set forth therein.

In the following claims, utility is emphasized by having the program simulation parallel a actual centrifugation. In order to distinguish the actual centrifugation from the simulated centrifugation, the term "actual centrifugation" has been used.

I claim:

1. A process for predicting the time of centrifugation and position-dependent separation of macromolecules of differing species in a gradient forming solution including a solute and solvent, the gradient forming occurring during centrifugation, said predicting process comprising the steps of;

computing the dimension of a cell relative to the spin axis of a rotor;

assuming placement in said cell of solvent, gradient forming solute and at least one species of macromolecule, said species having variable buoyancy with respect to said gradient forming solute in said solvent;

assuming rotation of said rotor to generate a centrifugal field for an increment of time;

determining for an increment of said cell at a fixed distance from the spin axis of said rotating rotor the density gradient produced by said gradient forming solute in said solvent in said centrifugal field during said increment of time;

determining from the buoyancy of said at least one specie of macromolecule a sedimentation coefficient for said macromolecule in said centrifugal field during said increment of time;

for each radial segment of said cell repeating for said increment of time said determining steps whereby the density gradient of said solute in said solvent and the separation state of said macromolecules relative to said segments are known for said increment of time;

repeating for successive increments of time said determining step whereby a quantitative estimation of the time dependent position of said solute density and macromolecule in said cell is obtained as a function of time.

2. The invention of claim 1 and including the step of:
mapping a model of said centrifugation to construct for discrete times discrete maps of the density of said solute and the separation of said macromolecules.

3. The process of claim 2 and including the steps of:
centrifuging in a centrifuge solvent, gradient forming solute, and at least one macromolecule;

and terminating said actual centrifugation at a time before equilibrium of said solvent, and said gradient forming solute is reached;

and utilizing said map to fractionate said centrifuge cell.

4. The process of claim 1 and including assuming rotation of said rotor to generate a first and larger centrifugal field wherein said gradient forming solute would precipitate out of said solvent at the end of a discrete time period;

assuming a lesser rotational speed of said rotor to generate a lesser centrifugal field before said discrete time period expires whereby said gradient forming solute in said solvent is accelerated in forming its gradient but not allowed to precipitate.

5. The process of claim 1 and including the steps of:
assuming placement of at least first and second species of macromolecules in said cell.

6. The process of claim 1 and wherein said cell is a cell in an analytical rotor, said cell having at least one wall with a window to permit interrogation of said cell during centrifugation.

7. The process of claim 4 and wherein said assuming rotation of said rotor to generate a first and larger centrifugal field wherein said gradient forming solvent would precipitate said gradient forming solute out of said solvent at the end of said discrete time period includes the steps of reducing rotation of said rotor at speeds which would precipitate out of said solvent in a plurality of discrete steps to reduce the speed at which the rotor runs gradually whereby the time of centrifugation can be reduced.

* * * * *